(12) United States Patent
Matsui et al.

(10) Patent No.: US 11,369,526 B2
(45) Date of Patent: Jun. 28, 2022

(54) DISPOSABLE DIAPER

(71) Applicant: UNICHARM CORPORATION, Ehime (JP)

(72) Inventors: Takashi Matsui, Kanonji (JP); Yasuhiro Yamanaka, Kanonji (JP); Satoru Sakaguchi, Kanonji (JP)

(73) Assignee: Unicharm Corporation, Ehime (JP)

( * ) Notice: Subject to any disclaimer, the term of this patent is extended or adjusted under 35 U.S.C. 154(b) by 11 days.

(21) Appl. No.: 17/136,632

(22) Filed: Dec. 29, 2020

(65) Prior Publication Data

US 2021/0113388 A1 Apr. 22, 2021

Related U.S. Application Data

(63) Continuation of application No. PCT/JP2019/025455, filed on Jun. 26, 2019.

(30) Foreign Application Priority Data

Jun. 29, 2018 (JP) .............................. JP2018-125576

(51) Int. Cl.
*A61F 13/49* (2006.01)
*A61F 13/511* (2006.01)
*A61F 13/53* (2006.01)
*A61F 13/56* (2006.01)
*A61F 13/494* (2006.01)

(52) U.S. Cl.
CPC ...... *A61F 13/49011* (2013.01); *A61F 13/511* (2013.01); *A61F 13/53* (2013.01); *A61F 13/56* (2013.01); *A61F 2013/49493* (2013.01)

(58) Field of Classification Search
CPC .............. A61F 13/49011; A61F 13/494; A61F 13/49466; A61F 13/495;
(Continued)

(56) References Cited

U.S. PATENT DOCUMENTS 6,280,426 B1* 8/2001 Turner .............. A61F 13/49466
604/385.101
6,336,922 B1* 1/2002 VanGompel ...... A61F 13/49011
604/385.29
(Continued)

FOREIGN PATENT DOCUMENTS

JP S64-026701 A 1/1989
JP H07-184954 A 7/1995
(Continued)

OTHER PUBLICATIONS

Office Action issued in corresponding Japanese Patent Application No. 2018-125576, dated Jul. 13, 2021 (8 pages).
(Continued)

*Primary Examiner* — Catharine L Anderson
*Assistant Examiner* — Lynne Anderson
(74) *Attorney, Agent, or Firm* — Osha Bergman Watanabe & Burton LLP

(57) ABSTRACT

A disposable diaper having a front-rear direction and a width direction that is orthogonal to the front-rear direction, includes: a front waistline region; a rear waistline region; a crotch region disposed between the front waistline region and the rear waistline region; an absorbent core; a skin surface side sheet disposed on a skin facing surface side from the absorbent core; a waistband disposed on the skin facing surface side of the skin surface side sheet in the rear waistline region; and a fastening tape disposed in the rear waistline region and that includes a locking portion.

13 Claims, 7 Drawing Sheets

(58) Field of Classification Search
CPC .. A61F 2013/49025; A61F 2013/49028; A61F 2013/4948; A61F 2013/49486; A61F 2013/49493
See application file for complete search history.

(56) References Cited

U.S. PATENT DOCUMENTS

| | | | | |
|---|---|---|---|---|
| 10,918,536 | B2* | 2/2021 | Inoue | A61F 13/49007 |
| 2003/0050616 | A1* | 3/2003 | Reynolds | A61F 13/49466 |
| | | | | 604/369 |
| 2018/0055698 | A1* | 3/2018 | Bishop | A61F 13/49466 |
| 2018/0071155 | A1 | 3/2018 | Bishop et al. | |

FOREIGN PATENT DOCUMENTS

| | | |
|---|---|---|
| JP | H07-184955 A | 7/1995 |
| JP | 2000-288013 A | 10/2000 |
| JP | 2000-513954 A | 10/2000 |
| JP | 2016-112341 A | 6/2016 |
| JP | 2016-187510 A | 11/2016 |
| JP | 2017-205569 A | 11/2017 |
| RU | 24771 U1 | 8/2002 |

OTHER PUBLICATIONS

International Search Report issued in corresponding International Application No. PCT/JP2019/025455 dated Sep. 17, 2019, with translation (4 pages).
Office Action issued in corresponding Japanese Patent Application No. 2018-125576 dated Mar. 9, 2021 (9 pages).
Office Action issued in corresponding Chinese Patent Application No. 201980044212.0, dated Sep. 3, 2021, with translation (13 pages).
Office Action issued in corresponding Russian Patent Application No. 2021101397, dated Jul. 16, 2021, with translation (11 pages).

* cited by examiner

DISPOSABLE DIAPER

BACKGROUND

Technical Field

The present invention relates to a disposable diaper having a waistband.

Related Art

A disposable diaper in which a waistband is disposed on a skin facing surface side of a skin surface side sheet in a rear waistline region has been known (refer to, for example, Patent Literature 1). In the waistband, a joining region joined to the skin surface side sheet is provided in a facing portion positioned closest to the skin surface side sheet. The waistband is folded back to the side away from the skin surface side sheet from a fold line, as a base point, extending in a width direction at a rear end edge of the joining region. The folded-back waistband is contracted by an elastic member to rise from the joining region of the waistband and the skin surface side sheet. A space interposed between the folded-back region and the joining region of the waistband forms a pocket which opens toward the front side. The pocket accommodates excrement moving toward a waist opening side.

Patent Literature 1: U.S. Patent Publication No. 2018/71155

In order to further suppress the occurrence of rear leakage in the disposable diaper of Patent Literature 1, it is considered to dispose the entire waistband closer to the waist opening side. In an example of a method of manufacturing a disposable diaper, a plurality of diapers is manufactured in a state of being continuous in the front-rear direction, and an end edge of the diaper in the front-rear direction is cut to obtain individual diapers. As described above, in the manufacturing method of cutting the end edge of the diaper in the front-rear direction, if the waistband is disposed close to the waist opening, the fold line of the waistband may be cut due to errors in a manufacturing process of the diaper, and a function as a pocket may not be exerted.

SUMMARY

One or more embodiments of the present invention provide a disposable diaper which can appropriately form a pocket due to a waistband and can suppress the occurrence of the rear leakage.

One or more embodiments of the present invention provide a disposable diaper having a front-rear direction and a width direction which are orthogonal to each other, including: a front waistline region, a rear waistline region, and a crotch region disposed between the front waistline region and the rear waistline region; an absorbent core; a skin surface side sheet positioned on a skin facing surface side from the absorbent core; a waistband disposed on the skin facing surface side of the skin surface side sheet in the rear waistline region; and a fastening tape disposed in the rear waistline region, in which a facing portion positioned closest to the skin surface side sheet in the waistband is provided with a joining region joined to the skin surface side sheet and a non-joining region to a front side from the joining region and not joined to the skin surface side sheet, a space interposed between the non-joining region and the skin surface side sheet in the waistband forms a pocket which opens toward the front side, and a rear end edge of the waistband is disposed on a rear side from a center of the waist region in the front-rear direction in a waist region positioned on the rear side from a locking arrangement region extending in the width direction from a locking portion of the fastening tape.

DETAILED DESCRIPTION

Figure 1:
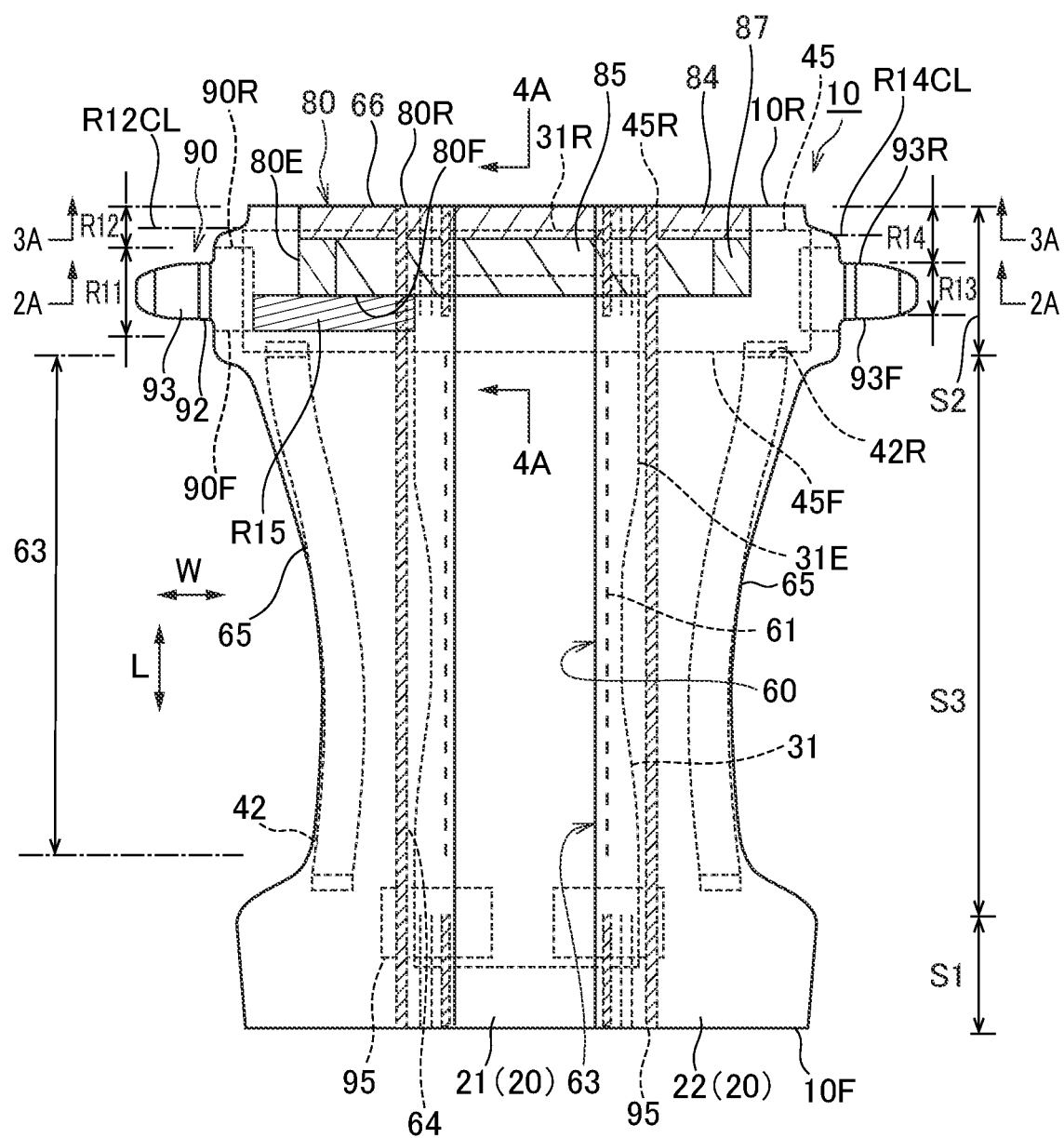
FIG. 1 is a schematic plan view of a disposable diaper according to a first embodiment when viewed from a skin facing surface side.

At least following matters will become clear with description of this specification and attached drawings. According to one or more embodiments, a disposable diaper having a front-rear direction and a width direction which are orthogonal to each other, including: a front waistline region, a rear waistline region, and a crotch region disposed between the front waistline region and the rear waistline region; an absorbent core; a skin surface side sheet positioned on a skin facing surface side from the absorbent core; a waistband disposed on the skin facing surface side of the skin surface side sheet in the rear waistline region; and a fastening tape disposed in the rear waistline region, in which a facing portion positioned closest to the skin surface side sheet in the waistband is provided with a joining region joined to the skin surface side sheet and a non-joining region to a front side from the joining region and not joined to the skin surface side sheet, a space interposed between the non-joining region and the skin surface side sheet in the waistband forms a pocket which opens toward the front side, and a rear end edge of the waistband is disposed on a rear side from a center of the waist region in the front-rear direction in a waist region positioned on the rear side from a locking arrangement region extending in the width direction from a locking portion of the fastening tape.

According to one or more embodiments, since the rear end edge of the waistband is disposed on the rear side from the center of the waist region in the front-rear direction, it is easy to secure the rigidity of the waist region. It is possible to suppress turning of the waist region, and to suppress rear leakage. In addition, the space interposed between the non-joining region in the facing portion of the waistband and the skin surface side sheet forms a pocket which opens toward the front side. A joining region is provided on the waist opening side from the non-joining region. Even if a part (for example, rear end edge) of the waistband is accidentally cut due to a manufacturing error or the like, the non-joining region is provided on the front side from the joining region, so that the function as a pocket is easily maintained. Therefore, it is possible to appropriately form a pocket due to a waistband and to suppress the occurrence of the rear leakage.

According to one or more embodiments, the rear end edge of the waistband may be disposed on the rear side from a center of a waist opening region in the front-rear direction in the waist opening region positioned on the rear side from a tape arrangement region extending from the fastening tape in the width direction.

According to one or more embodiments, since the rigidity is increased over a half or more of the length of the waist opening region in the front-rear direction, it is easy to secure the rigidity of the waist opening region. It is possible to suppress turning of the waist opening region, and to suppress rear leakage.

According to one or more embodiments, the waistband may have a folded-back portion folded to a side away from the skin surface side sheet from a fold line, as a base point, extending in the width direction at a front end edge of the non-joining region.

According to one or more embodiments, the folded-back portion is folded to the side away from the skin surface side sheet, and becomes a region in contact with the body. By providing the folded-back portion in contact with the body, it becomes easier to secure the accommodation space by the pocket.

According to one or more embodiments, the non-joining region is provided from the front end edge of the joining region to the fold line, and the length of the folded-back portion in the front-rear direction may be longer than the length of the non-joining region in the front-rear direction.

According to one or more embodiments, a length of the folded-back portion in contact with the body in the front-rear direction is longer than a length of the non-joining region constituting the accommodation space of the pocket. It is possible to secure a large area where the waistband is in contact with the body, and to enhance the stability of a shape of the waistband.

According to one or more embodiments, the rear end edge of the folded-back portion may be positioned on the rear side from the locking arrangement region.

According to one or more embodiments, the locking arrangement region is easily brought into close contact with the body in a wearing state. The folded-back portion is disposed on the waist opening side from the locking arrangement region which is in close contact with the body. The user can grasp that the pocket is disposed closer to the waist opening side, and can feel a sense of security with respect to the rear leakage.

According to one or more embodiments, the rear end edge of the folded-back portion may be positioned on the front side of the rear end edge of the joining region.

According to one or more embodiments, since the rear end edge of the folded-back portion is positioned on the front side from the rear end edge of the joining region, even if the folded-back portion is displaced at the time of manufacturing, it is possible to suppress the folded-back portion from being unintentionally cut.

According to one or more embodiments, a contractive force of the folded-back portion may be higher than a contractive force of the non-joining region.

According to one or more embodiments, since an expansion and contraction stress of the folded-back portion is relatively high, it is possible to secure the adhesion of the waistband to the body. Further, since the stress of the region where the non-joining region is provided is relatively low, it is possible to prevent the pocket from excessively rising from the body when the stress of the non-joining region is high, and to suppress the occurrence of a gap between the body and the pocket.

According to one or more embodiments, the rear end edge of the non-joining region may be positioned on the rear side from the center of the locking arrangement region in the front-rear direction.

According to one or more embodiments, the rear end edge of the non-joining region forms the rear end edge of the pocket interposed between the non-joining region of the facing portion and the skin surface side sheet. The length of the non-joining region in the front-rear direction can be secured, and a wide accommodation space of the pocket by the non-joining region can be provided.

According to one or more embodiments, the front end edge of the joining region may be positioned on the front side from the rear end edge of the locking arrangement region.

According to one or more embodiments, it is possible to secure the length of the joining region in the front-rear direction, increase the rigidity of the region where the waistband is disposed, and increase the rigidity of the waist region. Therefore, it is possible to suppress turning of the waist region, and to further suppress the rear leakage.

According to one or more embodiments, the rear end edge of the joining region may reach the rear end edge of the disposable diaper.

According to one or more embodiments, it is possible to increase the rigidity of the rear end edge of the disposable diaper, and it is easier to secure the rigidity of the waist region. It is possible to suppress turning of the waist opening region, and to suppress rear leakage.

According to one or more embodiments, there is provided a liquid-impermeable back-surface sheet positioned on the skin facing surface side from the absorbent core, in which at least a part of the back-surface sheet in a plan view of the disposable diaper may overlap with the joining region of the waistband.

Since at least a part of the back-surface sheet overlaps with the joining region of the waistband, leakage of body fluid from the accommodation space of the waistband to the non-skin surface side of the disposable diaper can be suppressed by the back-surface sheet. Further, it is possible to increase the rigidity of the region where the joining region is provided by the back-surface sheet, the rising portion of the waistband is more likely to rise with respect to the joining region, and thereby it is easier to form a pocket by the waistband.

Overall Schematic Configuration of Disposable Diaper

Hereinafter, a disposable diaper according to one or more embodiments will be described with reference to drawings. In the following description of the drawings, identical or similar portions will be given an identical or similar reference sign. However, it should be noted that the drawings are schematic and the ratios of the respective dimensions and the like are different from the reality. Therefore, specific dimensions and the like should be determined by taking into consideration of the following explanation. In addition, dimensional relationships or ratios between portions are not always identical among the drawings.

Figure 2:
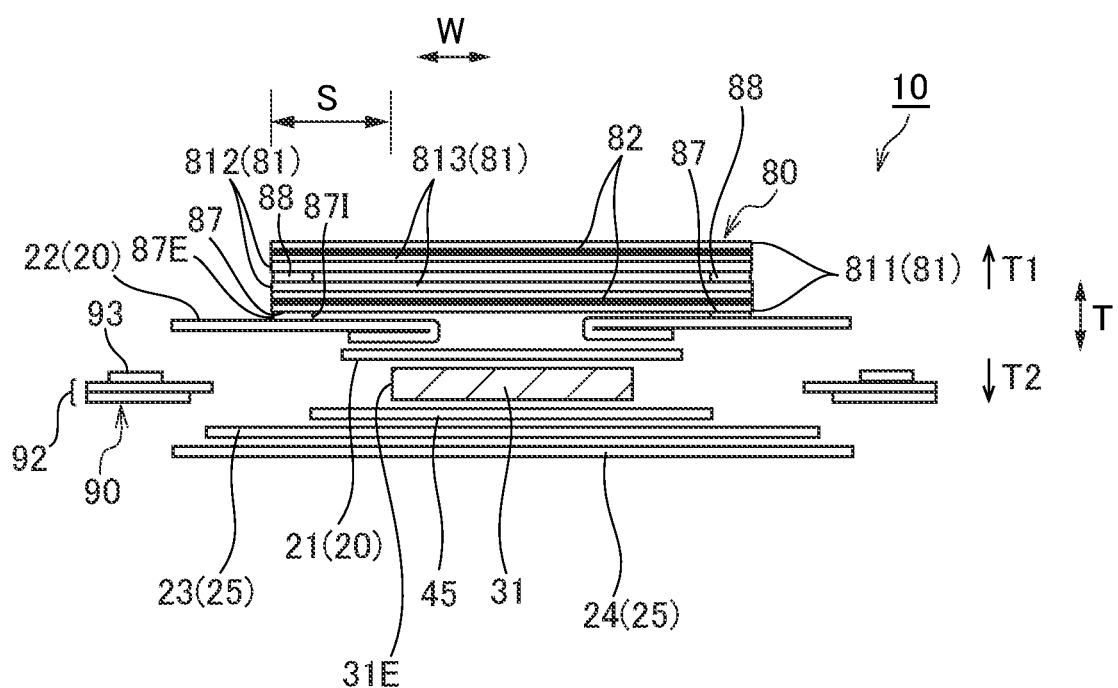
FIG. 2 is a schematic sectional view taken along line 2A-2A illustrated in FIG. 1.
Figure 3:
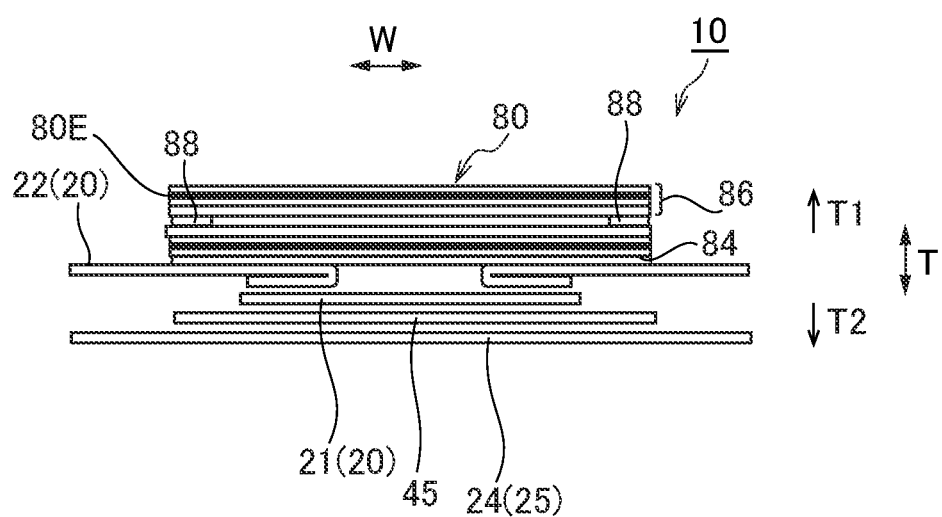
FIG. 3 is a schematic sectional view taken along line 3A-3A illustrated in FIG. 1.
Figure 4:
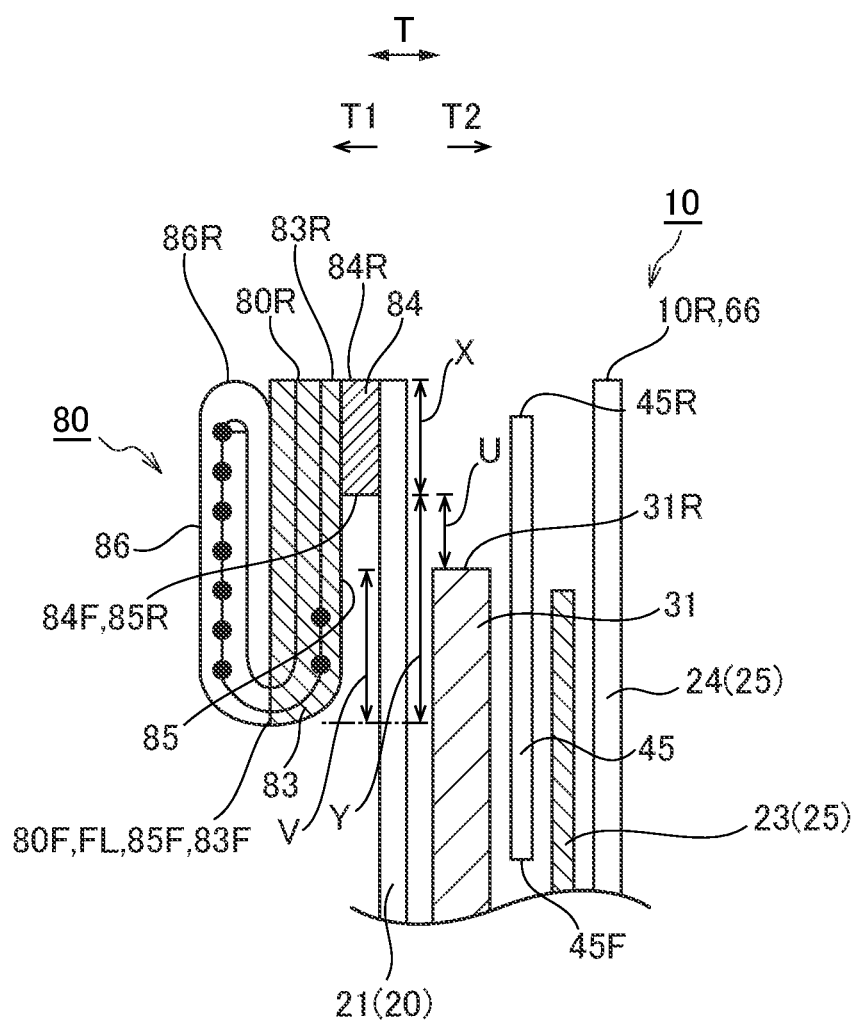
FIG. 4 is a schematic sectional view taken along line 4A-4A illustrated in FIG. 1 in a stretched state.
Figure 5:
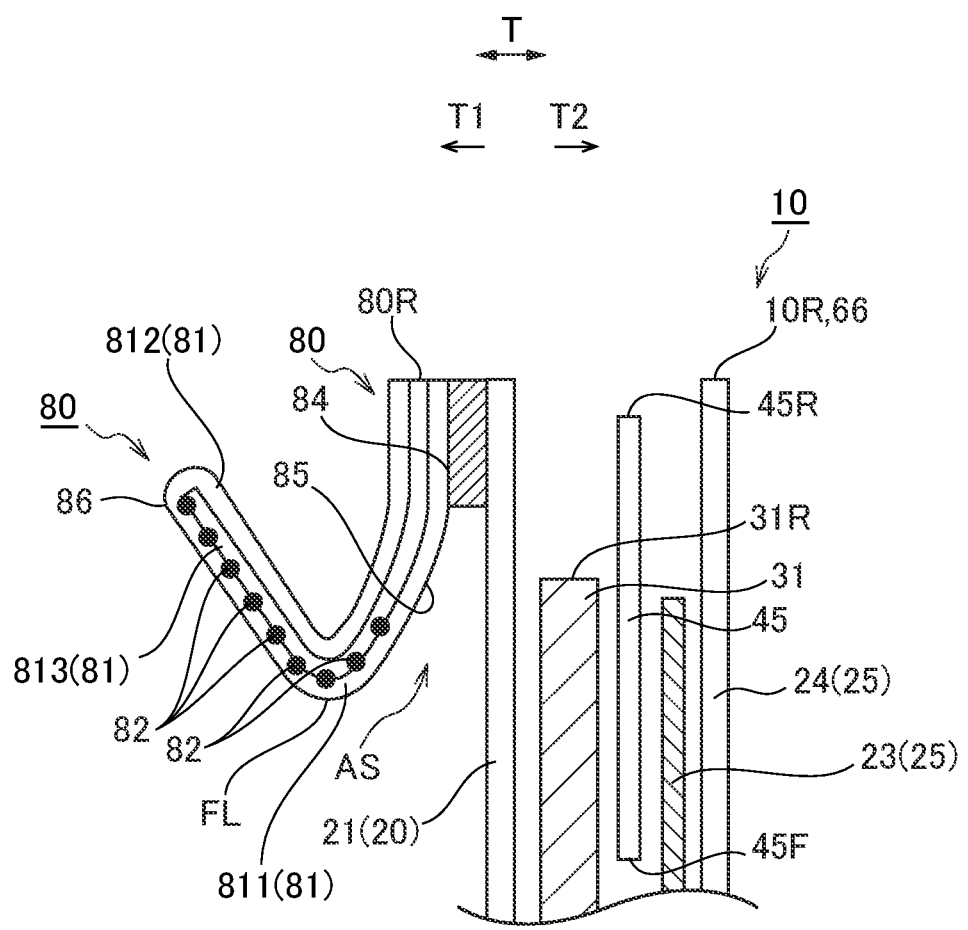
FIG. 5 is a schematic sectional view taken along line 4A-4A illustrated in FIG. 1 in a natural state.
Figure 6:
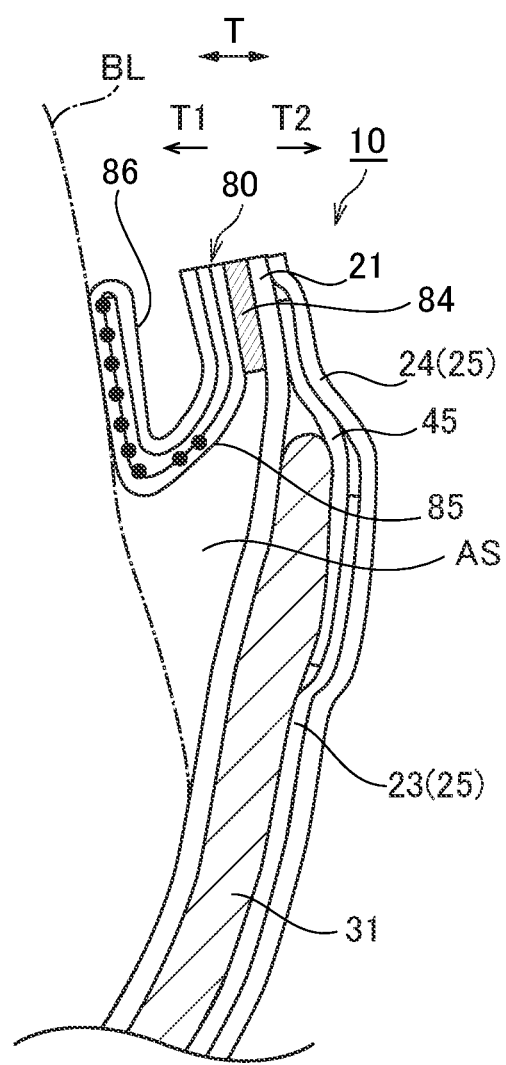
FIG. 6 is a diagram schematically illustrating a wearing state in a cross section with reference to FIG. 5.

The disposable diaper is a tape-type disposable diaper. FIG. 1 is a schematic plan view of a disposable diaper 10 according to a first embodiment when viewed from a skin facing surface side. FIG. 2 is a schematic sectional view taken along cross-section 2A-2A of the disposable diaper illustrated in FIG. 1. FIG. 3 is a schematic sectional view taken along cross-section 3A-3A of the disposable diaper illustrated in FIG. 1. FIGS. 1 to 3 illustrate a disposable diaper in a stretched state. The stretched state in one or more embodiments of the present invention is a state in which a disposable diaper 10 is stretched to a state in which no wrinkles are formed. In addition, the natural state in one or more embodiments of the present invention means a state that, in the case of the disposable diaper 10 accommodated in a package, the disposable diaper 10 is taken out of the package and left for 24 hours in an atmosphere of 20° C.±2° C. and relative humidity of 60%±5% RH. FIG. 4 is a schematic sectional view taken along line 4A-4A illustrated in FIG. 1 in a stretched state. FIG. 5 is a schematic sectional view taken along line 4A-4A illustrated in FIG. 1 in a natural state. In the schematic sectional view illustrated in FIGS. 2 to 5, for convenience of explanation, the respective members are illustrated separated in a thickness direction T, but are in contact with each other in the thickness direction T in an actual product. It is a diagram illustrating a wearing state with reference to the cross section illustrated in FIG. 5. BL illustrated in FIG. 6 represents a line of the wearer's body.

The disposable diaper 10 has a front-rear direction L and a width direction W orthogonal to each other. The front-rear direction L is defined by a direction extending toward the front side of the body and the rear side of the body. In other words, the front-rear direction L is a direction extending toward the front and the back in the unfolded disposable diaper 10. In addition, the disposable diaper 10 has a thickness direction T that is orthogonal to both the front-rear direction L and the width direction W. The thickness direction T extends to the skin facing surface side T1 toward the wearer side and the non-skin facing surface side T2 opposite to the skin facing surface side.

The disposable diaper 10 has a front waistline region S1, a rear waistline region S2, and a crotch region S3. The front waistline region S1 is a region that faces the front waistline (abdomen) of the wearer. The rear waistline region S2 is a region facing the rear waistline (back) of the wearer, and includes a region in which the body (buttocks) is placed when the wearer is worn. The crotch region S3 is a region that is positioned under the wearer's crotch and is disposed between the front waistline region S1 and the rear waistline region S2. The crotch region S3 is a region in which the leg openings 65 arranged around the leg of the wearer are provided. The leg opening 65 is a portion that is recessed inner side in the width direction from the outer side edge of the disposable diaper.

The disposable diaper 10 includes an absorbent core 31 including an absorbent material. The absorbent core 31 includes an absorbent material such as a pulverized pulp or a superabsorbent polymer (SAP), or a mixture thereof. The absorbent core 31 may be covered with a core wrap (not shown). The absorbent core 31 and the core wrap may form an absorbent body. The core wrap is form of a tissue or an SMS nonwoven fabric, and may be disposed on the skin facing surface side T1 of the absorbent core 31 and the non-skin facing surface side T2 of the absorbent core 31.

As illustrated in FIGS. 2 and 3, the disposable diaper 10 has a skin surface side sheet 20 positioned on the skin facing surface side T1 from the absorbent core 31. The skin surface side sheet 20 covers the absorbent core 31 and is disposed over the entire disposable diaper 10. The skin surface side sheet 20 of the present embodiment includes a top-surface sheet 21 and a pair of side sheets 22. In the disposable diaper having a core wrap, the skin surface side sheet 20 is a sheet positioned on the skin facing surface side T1 from the core wrap. The top-surface sheet 21 may be disposed so as to straddle the center of the absorbent core 31 in the width direction W. The side sheets 22 may be arranged so as to cover both outer side portions of the top-surface sheet 21. The top-surface sheet 21 and the side sheets 22 may be formed of a liquid-permeable sheet such as a nonwoven fabric or an apertured plastic film.

The inner side portion of the side sheet 22 may be folded back and overlapped. Between the overlapping side sheets 22, a leak-proof elastic member 61 that stretches and contracts in the front-rear direction L may be provided. The leak-proof elastic member 61 may be formed of an elastic string that stretches and contracts in the front-rear direction L. The side sheet 22 rises on the skin facing surface side T1 by contraction of the leak-proof elastic member 61. The side sheet 22 and the leak-proof elastic member 61 form a contraction portion 63 rising on the skin facing surface side T1. The leak-proof gather 60 has a contraction portion 63 and a leak-proof proximal edge 64 serving as a rising fulcrum of the contraction portion on the outer side of the contraction portion 63 in the width direction. The leak-proof proximal edge 64 is an inner side edge of a region where the side sheet and the top-surface sheet are joined to each other on the outer side of the contraction portion 63 in the width direction. The contraction portion 63 is a part in which the side sheet 22 is not joined to the top-surface sheet 21 and can be contracted by the leak-proof elastic member 61, and does not include a part in which the leak-proof elastic member 61 in the non-stretched state is disposed. The range of the contraction portion 63 in the front-rear direction is illustrated in FIG. 1.

The outer side portion in one or more embodiments of the present invention is a part occupying a certain range in the width direction W including an edge on the outer side in the width direction W, and the outer side edge is an edge on the outer side in the width direction W. Further, the inner side portion is a part occupying a certain range in the width direction W including an edge on the inner side in the width direction W, and the inner side edge is an edge on the inner side in the width direction W.

The disposable diaper 10 has a non-skin surface side sheet 25 positioned on the skin facing surface side T1 from the absorbent core 31. The non-skin surface side sheet 25 covers the absorbent core 31 and is disposed over the entire disposable diaper. The non-skin surface side sheet 25 of the present embodiment includes a back-surface sheet 23 and an exterior sheet 24. In the disposable diaper having a core wrap, the non-skin surface side sheet 25 is a sheet positioned on the non-skin facing surface side T2 from the core wrap. The back-surface sheet 23 is a liquid-impermeable sheet, and it is possible to use a polyethylene sheet, a laminated nonwoven fabric mainly containing polypropylene or the like, a breathable resin film, a sheet having a breathable resin film joined to a spunbond or spunlace nonwoven fabric, or the like. The exterior sheet 24 may be provided on the non-skin facing surface side T2 of the back-surface sheet 23. The exterior sheet 24 may be formed of a liquid-permeable nonwoven fabric. The length of the back-surface sheet 23 in the width direction W is shorter than the length of the exterior sheet 24 in the width direction W, the length of the back-surface sheet 23 in the front-rear direction L may be shorter than the length of the exterior sheet 24 in the front-rear direction L.

A fastening tape 90 is provided in the rear waistline region S2. The fastening tape 90 has a base portion 92 and a locking portion 93. At least a part of the base portion 92 is joined between the skin surface side sheet 20 and the non-skin surface side sheet 25, and extends outward in the width direction W from the skin surface side sheet 20 and the non-skin surface side sheet 25. The locking portion 93 is provided on the base portion 92 and is detachably fastened to the target portion 95 (refer to FIG. 1). The fastening tape 90 extends along the width direction W in the rear waistline region S2, and is fastened to the target portion 95, thereby holding the disposable diaper 10 to the wearer's body. The target portion 95 is disposed in the front waistline region S1 and is configured such that each fastening tape 90 is fastened thereto.

The disposable diaper 10 has a waistband 80 disposed on the skin facing surface side T1 of the skin surface side sheet 20 in the rear waistline region S2. The waistband 80 forms a pocket that rises from the skin surface side sheet 20 at the time of wearing and opens toward the front side. The pocket accommodates excrement moving toward a waist opening 66. The configuration of the waistband 80 will be described in detail later. The waist opening 66 is formed of a rear end edge 10R and a front end edge 10F of the disposable diaper, and is a part surrounding the waist-around in a state where the fastening tape 90 is fastened to the target portion 95.

The disposable diaper 10 has a tape arrangement region R11 extending in the width direction from the fastening tape 90, a waist opening region R12 positioned on the rear side from the tape arrangement region R11, a locking arrangement region R13 extending in the width direction from the locking portion 93 of the fastening tape, and a waist region R14 positioned on the rear side from the locking arrangement region R13. The range of each of the regions R11 to R14 in the front-rear direction L is illustrated in FIG. 1. The tape arrangement region R11 is a region between a front end edge 90F and a rear end edge 90R of the fastening tape in the front-rear direction L. Thus, the front end edge of the tape arrangement region R11 corresponds to the front end edge 90F of the fastening tape 90, and the rear end edge of the tape arrangement region R11 corresponds to the rear end edge 90R of the fastening tape 90. The waist opening region R12 is a region between the rear end edge 90R of the fastening tape 90 and the rear end edge 10R of the disposable diaper 10 in the front-rear direction L. Thus, the front end edge of the waist opening region R12 corresponds to the rear end edge 90R of the fastening tape, and the rear end edge of the waist opening region R12 corresponds to the rear end edge 10R of the disposable diaper 10. The locking arrangement region R13 is a region between the front end edge 93F and the rear end edge 93R of the locking portion 93 in the front-rear direction L. Thus, the front end edge of the locking arrangement region R13 corresponds to the front end edge 93F of the locking portion 93, and the rear end edge of the locking arrangement region R13 corresponds to the rear end edge 93R of the locking portion 93. The waist region R14 is a region between the rear end edge 93R of the locking portion 93 and the rear end edge 10R of the disposable diaper 10 in the front-rear direction L. Thus, the front end edge of the waist region R14 corresponds to the rear end edge 93R of the locking portion 93, and the rear end edge of the waist region R14 corresponds to the rear end edge 10R of the disposable diaper 10.

Between the side sheet 22 and the back-surface sheet 23, or between the side sheet 22 and the exterior sheet 24, a leg-around elastic member 42 extending in the front-rear direction L may be provided. The leg-around elastic member 42 may be formed of a band-like stretching/contracting sheet that stretches and contracts in the front-rear direction L. The contraction of the leg-around elastic member 42 causes the disposable diaper 10 to fit the leg-around at the time of wearing. The leg-around elastic member 42 is disposed along the leg opening 65 at least in the crotch region S3 on the outer side from the absorbent core 31 in the width direction W. The leg-around elastic member 42 is disposed between the exterior sheet 24 and the side sheet 22, and between the back-surface sheet 23 and the side sheet 22.

Between the side sheet 22 and the back-surface sheet 23, and between the side sheet 22 and the exterior sheet 24, a waist-around elastic member 45 extending in the width direction W may be provided. The waist-around elastic member 45 may be formed of a substantially rectangular stretching/contracting sheet that stretches and contracts in the width direction W. The waist-around elastic member 45 is joined between the skin surface side sheet 20 and the non-skin surface side sheet 25. More specifically, as illustrated in FIG. 4, the waist-around elastic member 45 is joined between the absorbent core 31 and the non-skin surface side sheet 25 or between the skin surface side sheet 20 and the non-skin surface side sheet 25 in a state of being stretched state in the width direction W. The contraction of the waist-around elastic member 45 causes the disposable diaper 10 to fit the waist-around at the time of wearing. The waist-around elastic member 45 is disposed at least in the rear waistline region S2. The waist-around elastic member 45 is disposed to straddle the locking arrangement region R13 and the waist region R14. The rear end edge 45R of the waist-around elastic member 45 is positioned on the front side from the rear end edge 10R and on the rear side of the tape arrangement region R11 of the disposable diaper 10. The front end edge 45F of the waist-around elastic member 45 is positioned on the front side from the tape arrangement region R11 and on the front side of the rear end edge 31R of the absorbent core 31. The waist-around elastic member 45 is disposed so as to overlap with any one of the skin surface side sheet 20 and the non-skin surface side sheet 25, and forms a reinforcing sheet according to one or more embodiments of the present invention. The reinforcing sheet is a sheet separate from the skin surface side sheet 20 and the non-skin surface side sheet 25, and reinforces a region where the skin surface side sheet 20 and the non-skin surface side sheet 25 are disposed. In the present embodiment, the state in which the two members overlap with each other includes not only a state in which the two members are in contact and overlap with each other, but also a state in which other members are arranged between the two members and the two members overlap indirectly.

Configuration of Waistband

Next, the configuration of the waistband 80 will be described in detail. As illustrated in FIG. 5, the waistband 80 has a sheet layer 81 in which a plurality of sheets is stacked, and a band elastic member 82 joined to the sheet layer 81. The sheet layer 81 of the waistband 80 of the present embodiment includes a first nonwoven fabric layer 811, a second nonwoven fabric layer 812, and a film layer 813 disposed between the first nonwoven fabric layer 811 and the second nonwoven fabric layer 812. The first nonwoven fabric layer 811 and the second nonwoven fabric layer 812 are formed of the same nonwoven fabric and are folded back at an apex of the folded-back portion 86 of the waistband 80. The first nonwoven fabric layer 811 is positioned closest to the skin surface side sheet 20 in the waistband 80.

The band elastic member 82 is formed of a thread-like or band-like elastic member, and is fixed to the sheet layer 81 in the stretched state in the width direction W. The band elastic member 82 of the present embodiment is fixed between the first nonwoven fabric layer 811 and the film layer 813. A plurality of the band elastic members 82 are arranged at intervals in the front-rear direction L. The plurality of band elastic members 82 are arranged in each of the non-joining portion 85 and the folded-back portion 86 to be described later.

The waistband 80 may be disposed in the vicinity of the waist opening 66 in the rear waistline region S2. An outer side edge 80E of the waistband 80 may be positioned on the outer side from an outer side edge 31E of the absorbent core 31 in the width direction and may be positioned on the inner side from the inner side edge of the fastening tape 90 in the width direction. The front end edge 80F of the waistband 80 may be positioned on the rear side from the front end edge 90F of the fastening tape 90. The front end edge 80F of the waistband 80 may be positioned on the front side from the rear end edge 90R of the fastening tape 90. Since the fastening tape 90 and the waistband 80 overlap with each other in the width direction W, the interlocking property between the fastening tape 90 and the waistband 80 can be enhanced. The front end edge 80F of the waistband 80 may be disposed on the rear side from the center of the fastening tape 90 in the front-rear direction L. The waistband 80 is provided on the waist opening side, and an accommodation space AS of the waistband can be widely provided.

The disposable diaper 10 has a space region R15 between the front end edge 90F of the fastening tape 90 and the front end edge 80F of the waistband 80 in the front-rear direction L, and between the inner side edge of the fastening tape and the outer side edge of the absorbent core 31 in the width direction W. The space region R15 may be positioned on both sides of the absorbent core 31 in the width direction. The one space region R15 and the other space region R15 may be disposed at intervals in the width direction W. In FIG. 1, the space region R15 is indicated by hatching.

The waistband 80 has a rising portion configured to rise with respect to the skin surface side sheet 20, and a proximal edge serving as a rising fulcrum of the rising portion. The proximal edge has a first proximal edge positioned on the outer side from the absorbent core 31 in the width direction, and a second proximal edge positioned on the waist opening 66 side from the rising portion.

The waistband 80 is configured to be able to stretch and contract in the width direction W. The waistband 80 may be configured to stretch and contract in the width direction by the band elastic member 82, or may be configured to stretch and contract in the width direction by the stretchability of the sheet layer. The waistband 80 may be configured so that at least a rising portion is contractible, and the entire rising portion, the first proximal edge, and the second proximal edge may be configured to be contractible.

The waistband 80 has a facing portion 83 positioned closest to the skin surface side sheet 20 in the waistband 80. The facing portion 83 is formed of a part that can be in contact with the skin surface side sheet 20, includes the sheet layer 81 positioned closest to the skin surface side sheet 20, and is not folded back from the fold line as a base point. The facing portion 83 of the present embodiment is a part that is not folded back with respect to a fold line FL, and is configured of a part that is positioned on the skin facing surface side and the rear side from the fold line FL. In FIG. 4, the facing portion 83 is indicated by hatching. The facing portion 83 is provided with a joining portion 84 joined to the skin surface side sheet 20, and a non-joining portion 85 extending to the front side from the joining portion 84 and not joined to the skin surface side sheet 20. In FIG. 4, a length X of the joining portion 84 in the front-rear direction and a length Y and the non-joining portion 85 in the front-rear direction L are indicated. The joining portion 84 forms a joining region according to one or more embodiments of the present invention, and the non-joining portion 85 forms a non-joining region according to one or more embodiments of the present invention.

As illustrated in FIGS. 5 and 6, the accommodation space AS interposed between the non-joining portion 85 of the waistband 80 and the skin surface side sheet 20 forms a pocket which opens toward the front side. Therefore, the non-joining portion 85 forms a rising portion according to one or more embodiments of the present invention. The front end edge of the rising portion is the front end edge 85F of the non-joining portion 85, and the rear end edge of the rising portion is the rear end edge 85R of the non-joining portion 85. The front end edge 85F of the non-joining portion 85 may be positioned on the front side from the rear end edge 31R of the absorbent core 31 in the stretched state. The joining portion 84 extends to the rear side from the non-joining portion 85. The front end edge 84F of the joining portion 84 forms a second proximal edge according to one or more embodiments of the present invention. The joining portion 84 extends in the front-rear direction from the second proximal edge. The rear end edge 84R of the joining portion 84 may extend to the rear end edge 80R of the waistband 80 and may correspond to the rear end edge 10R of the disposable diaper 10. The front end edge 84F of the joining portion 84 forms a rear end edge of the pocket. The front end edge 84F of the joining portion 84 may be positioned on the rear side from the rear end edge 31R of the absorbent core 31 in the stretched state, or may correspond to the rear end edge 31R of the absorbent core 31. In the disposable diaper 10 of the present embodiment, the positions of the rear end edge 84R of the joining portion 84, the rear end edge 83R of the facing portion 83, the rear end edge 80R of the waistband, and the rear end edge 10R of the disposable diaper 10 correspond to each other in the front-rear direction L.

If the rear end edge 84R of the joining portion 84 is configured to be positioned on the front side from the rear end edge 80R of the waistband 80, the non-joining portion may be provided on the rear side from the joining portion 84. The non-joining portion positioned on the rear side from the joining portion 84 does not open toward the front side to form a pocket. Therefore, even if the pocket is erroneously cut due to an error in a manufacturing process described later, the formation of the pocket is not affected. In addition, the non-joining portion positioned on the rear side from the joining portion 84 may be folded on the side away from the skin surface side sheet 20 from a fold line, as a base point, extending in the width direction at the rear end edge of the non-joining portion.

The waistband 80 has a side joining portion 87 joined to the skin surface side sheet 20 on the outer side from the non-joining portion 85 forming the rising portion the width direction. The outer side edge 87E of the side joining portion 87 may be disposed in the vicinity of the outer side edge 80E of the waistband 80 and may reach the outer side edge 80E of the waistband 80. An inner side edge 87I of the side joining portion 87 may be positioned on the outer side from the outer side edge 31E of the absorbent core 31 in the width direction W, and is spaced apart from the absorbent core 31 in the width direction W. The inner side edge 87I of the side joining portion 87 forms the first proximal edge according to one or more embodiments of the present invention. In FIG. 1, the non-joining portion 85, the side joining portion 87, and the joining portion 84 forming the rising portion is indicated by different hatch lines.

The non-joining portion 85 extends to the front side from the joining portion 84. The waistband 80 may have a folded-back portion 86 folded back around the fold line FL as a base point extending in the width direction W at the front end edge 85F of the non-joining portion 85. The non-joining portion 85 is provided from the front end edge 84F of the joining portion 84 to the fold line FL. The front end edge 85F of the non-joining portion 85 forms the front end edge 83F of the facing portion 83 and the front end edge 80F of the waistband 80, and corresponds to the fold line FL. The length of the non-joining portion 85 in the front-rear direction L is a distance between the front end edge 84F of the joining portion 84 and the fold line FL. As illustrated in FIG. 6, the folded-back portion 86 is folded to the side away from the skin surface side sheet 20, and becomes a region in contact with a body. By providing the folded-back portion 86 in contact with the body, it becomes easier to secure the accommodation space by the pocket. The waistband 80 according to a modified example may not have the folded-back portion 86.

The folded-back portion 86 extends to the rear side from the front end edge 85F of the non-joining portion 85. In the stretched state, the rear end edge 86R of the folded-back portion 86 may correspond to the rear end edge 83R of the facing portion 83, may be on the front side from the rear end edge 83R of the facing portion 83, or may be on the rear side from the rear end edge 83R of the facing portion 83. In the present embodiment, the rear end edge 86R of the folded-back portion 86 correspond to the rear end edge 83R of the facing portion 83 in the front-rear direction L. If the rear end edge 86R of the folded-back portion 86 is configured to be positioned on the front side from the rear end edge 83R of the facing portion 83, the rear end edge 83R of the facing portion 83 forms the rear end edge 80R of the waistband 80. If the rear end edge 86R of the folded-back portion 86 is configured to be positioned on the rear side from the rear end edge 83R of the facing portion 83, the rear end edge 86R of the folded-back portion 86 forms the rear end edge 80R of the waistband 80.

As illustrated in FIGS. 2 and 3, an outer side portion of the folded-back portion 86 is joined via a second joining portion 88 with respect to a part (facing portion 83) of the waistband which is not folded-back. The second joining portion 88 is provided in a pair on both sides of the folded-back portion 86 in the width direction. In the region between the pair of second joining portions 88, the folded-back portion 86 rises on the wearer side with respect to the facing portion 83.

The waistband according to the modified example may be folded back to the side away from the skin surface side sheet 20 from a fold line, as a base point, extending in the width direction W at the rear end edge 86R of the folded-back portion 86. The folded-back portion 86 is further folded, so that the waistband 80 rises closer to the wearer side, and the waistband 80 is more easily brought into contact with the body.

The front end edge 80F of the waistband 80 may be positioned in the tape arrangement region R11 or in the locking arrangement region R13 in the stretched state. That is, the front end edge 80F of the waistband 80 may be positioned on the front side from the front end edge of the waist region R14, or may be positioned on the front side from the front end edge of the waist opening region R12.

The rear end edge 80R of the waistband 80 is disposed on the rear side from a center R14CL in the front-rear direction of the waist region R14 in the stretched state. The waist region R14 is positioned on the rear side from the locking arrangement region R13. The locking arrangement region R13 is a region for holding the disposable diaper 10 with respect to the body in a state in which the locking portion 93 is fastened to the target portion 95 at the time of wearing. The waist region R14, which is positioned on the rear side from the locking arrangement region R13, is less likely to receive a force for holding it around the waistline of the wearer with the fastening tape 90 or the like, and the waist region R14 is relatively easily deformed in the rear waistline region S2. The rigidity of the waist region R14 can be increased by disposing the waistband 80 in the waist region R14. The waistband 80 is disposed half or more of the length of the waist region R14 in the front-rear direction L. Therefore, the rigidity is increased over a half or more of the length of the waist region R14 in the front-rear direction L, and the rigidity of the waist region R14 is easily secured. It is possible to suppress turning of the waist region R14, and to suppress rear leakage.

In addition, the pocket of the waistband 80 is formed by the accommodation space AS interposed between the non-joining portion 85 of the facing portion 83 and the skin surface side sheet 20. The joining portion 84 is provided on the waist opening 66 side from the non-joining portion 85. Since the non-joining portion 85 is provided on the front side from the joining portion 84, a part (for example, the rear end edge of the waistband 80) of the waistband 80 by such manufacturing errors is accidentally cut, the pocket is less likely to be cut. Therefore, a function as a pocket can be easily maintained, the pocket formed by the waistband 80 can be appropriately formed, and the occurrence of rear leakage can be suppressed.

The rear end edge 80R of the waistband 80 may be disposed on the rear side of a center R12CL of the waist opening region R12 in the front-rear direction L in the stretched state. The waist opening region R12 is positioned on the rear side from the tape arrangement region R11. The tape arrangement region R11 is a region for holding the disposable diaper with respect to the body in a state in which the fastening tape 90 is fastened to the target portion 95 at the time of wearing. The waist opening region R12, which is positioned on the rear side of the tape arrangement region R11, is less likely to receive a force for holding it around the waistline of the wearer, and the waist opening region R12 is more easily deformed in the rear waistline region S2. In addition, when the disposable diaper configured as described above is worn on a wearer in a sleeping state, the rear waistline region S2 may be inserted between the body of the wearer and the bedding or the like. At this time, the waist opening region R12 is positioned at the tip at the time of insertion, and is a region easily turned or tucked. The rigidity of the waist opening region R12 can be increased by disposing the waistband 80 in the waist opening region R12. The waistband 80 is disposed half or more of the length of the waist opening region R12 in the front-rear direction L. Therefore, the rigidity is increased over a half or more of the length of the waist opening region R12 in the front-rear direction L, and the rigidity of the waist opening region R12 is easily secured. It is possible to suppress turning of the waist opening region R12, and to suppress rear leakage.

The rear end edge 84R of the joining portion 84 may be disposed on the rear side from the center R14CL in the front-rear direction of the waist region R14 in the stretched state. The joining portion 84 is a region joined to the skin surface side sheet 20, and can further increase the rigidity of the waist region R14. Therefore, the effect of increasing the rigidity of the waist region R14 and suppressing the rear leakage can be more easily obtained. The rear end edge 84R of the joining portion 84 may be disposed on the rear side from the center R12CL in the front-rear direction of the waist opening region R12 in the stretched state. The effect of increasing the rigidity of the waist opening region R12 and suppressing the rear leakage can be more easily obtained. The rear end edge 84R of the joining portion 84 may reach the rear end edge 10R of the disposable diaper 10 in the stretched state. It is possible to increase the rigidity of the rear end edge 10R of the disposable diaper 10, and it is easier to secure the rigidity of the waist opening region R12. It is possible to suppress turning of the waist opening region R12, and to more suppress the rear leakage.

The rear end edge 85R of the non-joining portion 85 may be positioned on the rear side from the center of the locking arrangement region R13 in the front-rear direction L in the stretched state. The rear end edge 85R of the non-joining portion 85 forms the rear end edge of the pocket interposed between the non-joining portion 85 of the facing portion 83 and the skin surface side sheet 20. The length of the non-joining portion 85 in the front-rear direction L can be secured, and a wide accommodation space of the pocket by the non-joining portion 85 can be provided.

The front end edge 84F of the joining portion 84 may be positioned on the front side from the rear end edge of the locking arrangement region R13 in the stretched state. It is possible to secure the length of the joining portion 84 in the front-rear direction L, and more increase the rigidity of the region where the waistband 80 is disposed. Therefore, it is possible to further suppress turning of the waist region R14, and to suppress the rear leakage.

The waist-around elastic member 45 as a reinforcing sheet may be disposed in the waist region R14. The waist-around elastic member 45 may be disposed half or more of the length of the waist region R14 in the front-rear direction L. Therefore, the rigidity is increased over a half or more of the length of the waist region R14 in the front-rear direction L, and the rigidity of the waist region R14 is easily secured. It is possible to suppress turning of the waist region R14, and to suppress rear leakage. The waist-around elastic member 45 as a reinforcing sheet may be disposed in the waist opening region R12. It is possible to suppress turning of the waist opening region R12, and to suppress rear leakage.

The waist-around elastic member 45 may be disposed to straddle the left and right fastening tapes 90. A region of high rigidity is provided continuously in the width direction by the fastening tape 90 and the waist-around elastic member 45. Therefore, it is possible to suppress the tucking in the vicinity of the waist opening in the rear waistline region, and it is possible to further suppress the leakage in the rear waistline region.

A waist-around elastic member 45 as a reinforcing sheet may be provided in the space region R15 of the disposable diaper. The region between the waistband 80 and the fastening tape 90 in the width direction W is reinforced by the waist-around elastic member 45, and the fastening tape 90 and the waistband 80 is easily interlocked. Therefore, when the fastening tape 90 is pulled to the outside of the width direction W, the waistband 80 is interlocked and pulled in the width direction W, and the waistband 80 is easily risen from the skin surface side sheet 20. The waistband 80 facilitates the pocket formation.

Further, the front end edge 80F of the waistband 80 is positioned closer to the waist opening 66 side from the front end edge 90F of the fastening tape 90, and in the wearing state, the waistband 80 easily covers the buttocks and easily accommodates the excrement from the buttocks. At this time, a region between the front end edge 80F of the waistband 80 and the front end edge 90F of the fastening tape 90 in the front-rear direction L is reinforced by the waist-around elastic member 45, so that it is difficult to deform and wrinkles are less likely to be generated. Therefore, it is possible to suppress the waistband 80 from being pulled down to the crotch side due to the deformation between the front end edge 80F of the waistband 80 and the front end edge 90F of the fastening tape 90 in the front-rear direction L. Therefore, it is possible to continuously cover the buttocks by the waistband 80, and it is possible to suppress the rear leakage.

The waist-around elastic member 45 may be disposed in at least a part of the space region R15. The length of the waist-around elastic member 45 disposed in the space region R15 in the width direction W may be ½ or more of the length of the space region R15 in the width direction W. That is, in each of the space regions R15, the waist-around elastic member 45 may be disposed over ½ or more of the length of the space region R15 in the width direction W. In addition, the length of the waist-around elastic member 45 disposed in the space region R15 in the front-rear direction L may be ½ or more of the length of the space region R15 in the front-rear direction L. That is, in each of the space regions R15, the waist-around elastic member 45 may be disposed over ½ or more of the length of the space region R15 in the front-rear direction L. The rigidity of the space region R15 can be further increased by the waist-around elastic member 45 to suppress the waistband 80 from being pulled down to the crotch side, and the waistband 80 can more easily rise by the interlocking with the fastening tape 90. In the present embodiment, the waist-around elastic member 45 is disposed in the entire region of the space region R15, and deformation of the entire region of the space region R15 can be suppressed.

The waist-around elastic member 45 as a reinforcing sheet may have stretchability in which at least a part stretches and contracts in the width direction W. When the waist-around elastic member 45 stretches and contracts in the width direction W, it is possible to increase the interlocking performance of the fastening tape 90 and the waistband 80 at the time of wearing. In addition, when the waist-around elastic member 45 is extended in a state in which the wearer is in a frontward bending posture, the rear waistline region S2 can follow the body, and the rear waistline region S2 can continue to fit the body. In addition, a part where the space region R15 is applied to the wearer is a part which is on the upper side from the bulge of the buttocks of the wearer and is recessed in the body. In addition, in the space region R15, the absorbent core 31 is not disposed, and a gap with the body tends to occur. By contracting at least a part of the space region R15 in which the gap is likely to be generated by the waist-around elastic member 45, it is possible to suppress that the rear waistline region S2 fits the body and a gap between the body and the diaper is generated. The reinforcing sheet may have the stretchability over the entire region. In the modified example, the reinforcing sheet may not have the stretchability.

The waist-around elastic member 45 may overlap with the waistband 80 in the thickness direction T. The waist-around elastic member 45 and the waistband 80 are more easily interlocked with each other, and when the fastening tape 90 is pulled at the time of wearing, the waistband 80 is interlocked to be pulled via the waist-around elastic member 45, thereby making it easier to form a pocket by the waistband 80.

The waist-around elastic member 45 may overlap with at least a part of the waistband 80, and may overlap with the entire region of the waistband 80. The force pulled in the width direction W over the entire waistband 80 in the width direction W can be transmitted. In addition, the waistband 80 rises on the wearer side with respect to the skin surface side sheet 20 and the waist-around elastic member 45 in the thickness direction T. The rigidity of the waistband 80 on the base side at the time of rising is increased, and the waistband 80 more easily rises on the wearer side.

In addition, the waist-around elastic member 45 may overlap with the fastening tape 90 in the thickness direction T. When pulling the fastening tape 90 at the time of wearing, the force pulling to the outside of the width direction W is easily applied to the waist-around elastic member 45. The waistband 80 can be interlocked and pulled via the waist-around elastic member 45, thereby making it easier to form a pocket by the waistband 80. The waist-around elastic member 45 may overlap with at least a part of the base portion 92 of the fastening tape 90.

The waist-around elastic member 45 may extend to the front side from the front end edge 90F of the fastening tape 90. The region on the crotch side from the fastening tape 90 is easily deformed by a force exerted by the movement of the wearer or the like. Even in the region of the crotch region side from the fastening tape 90, the rigidity is increased by the waist-around elastic member 45, and thereby it is possible to suppress the deformation.

The area of the region where the waistband 80 and waist-around elastic member 45 overlaps with each other may be larger than the area of the region where the fastening tape 90 and waist-around elastic member 45 overlap with each other. The fastening tape 90 is disposed in the same layer as the waist-around elastic member 45 in the thickness direction T, and the fastening tape 90 and the waist-around elastic member 45 are relatively easy to interlock. On the other hand, the waistband 80 is disposed on the skin facing surface side of the skin surface side sheet 20, and is disposed so as to be deviated from the waist-around elastic member 45 in the thickness direction T. By increasing the area of the region where the waistband 80 and the waist-around elastic member 45 overlap with each other, the interlocking property between the waist-around elastic member 45 and the waistband 80 can also be enhanced.

The distance between the rear end edge 90R of the fastening tape 90 and the front end edge 80F of the waistband 80 may be shorter than the distance between the front end edge 90F of the fastening tape 90 and the front end edge 80F of the waistband 80. That is, the front end edge 80F of the waistband 80 is positioned on the rear side from the center of the fastening tape 90 (the center of the tape arrangement region) in the front-rear direction L. When the waistband 80 is disposed in the vicinity of the waist opening 66 side, the buttocks can be covered more easily, and the leakage of excrement can be suppressed. In addition, since the space region R15 can be reinforced by the waist-around elastic member 45, even if the waistband 80 is disposed in the vicinity of the waist opening 66 side, the waistband 80 is suppressed from being pulled down to the crotch side, and the pocket by the waistband 80 can be continuously disposed on the upper side of the buttocks.

The waist-around elastic member 45 may be disposed in a region which does not overlap with the leg-around elastic member 42 in the thickness direction T. It is possible to suppress tucking of the waist-around elastic member 45 due to contraction of the leg-around elastic member 42, and it is easier to obtain an effect of suppressing deformation of the space region R15 by the waist-around elastic member 45.

The waist-around elastic member 45 may be disposed in a region extending to the rear side from the rear end edge 42R of the leg-around elastic member 42 along the front-rear direction L. The region extending to the rear side along the front-rear direction L from the rear end edge of the leg-around elastic member 42 is a region extending to the rear side along the front-rear direction L from the rear end edge 42R of the leg-around elastic member 42 disposed in the stretched state (not including the leg-around elastic member disposed in a non-stretched state). FIG. 1 illustrates the rear end edge 42R of the leg-around elastic member 42 disposed in the stretched state. The region extending to the rear side from the rear end edge of the leg-around elastic member 42 is easily pulled down to the crotch region side by contraction of the leg-around elastic member 42. A region extending to the rear side along the front-rear direction L from the rear end edge 42R of the leg-around elastic member 42 is reinforced by the waist-around elastic member 45, and is difficult to be pulled down to the crotch region side. It is possible to suppress the waistband 80 from being pulled down to the crotch side. Therefore, it is possible to continuously cover the buttocks by the waistband 80, and it is possible to suppress the rear leakage.

The waist-around elastic member 45 may overlap with the proximal edge of the waistband 80 in the thickness direction T. In the present embodiment, the waist-around elastic member 45 overlaps with the inner side edge 87I of the side joining portion 87 as a first proximal edge and the front end edge 84F of the joining portion 84 as a second proximal edge. The waist-around elastic member 45 may overlap with at least a part of the proximal edge of the waistband 80, and may overlap with the entire region of the proximal edge of the waistband 80. When pulling the fastening tape 90 at the time of wearing, the proximal edge of the waistband 80 can be interlocked and pulled via the waist-around elastic member 45. As the proximal edge of the waistband 80 is pulled, the rising portion of the waistband 80 more easily rises, thereby making it easier to form a pocket by the waistband 80.

The waist-around elastic member 45 may be disposed to straddle one space region R15 and the other space region R15. One waist-around elastic member 45 can reinforce both the one space region R15 and the other space region R15. Further, when the waist-around elastic member 45 is continuously disposed in the region between the left and right fastening tape 90 in the width direction W, it is possible to increase the interlocking property of the left and right fastening tape 90. Therefore, it is possible to suppress that the rear waistline region S2 more fits to the body and a gap is formed between the body and the diaper.

The waistband 80 may be disposed in a region which does not overlap with the contraction portion 63 of the leak-proof gather 60 in the thickness direction T. It is possible to suppress tucking of the waist-around elastic member 45 due to contraction of the contraction portion 63, and it is easier to obtain an effect of suppressing deformation of the space region R15 by the waist-around elastic member 45.

A tensile load of the waistband 80 in the width direction W may be lower than the tensile load of the waist-around elastic member 45 in the width direction W. When it is pulled outward in the width direction W at the time of wearing, the waistband 80 extends first, and then the waist-around elastic member 45 extends. The waistband 80 is likely to extend and rise on the body side more easily. Therefore, the waistband 80 more fits to the body, and the rear leakage can be further suppressed.

The tensile load of the leg-around elastic member 42 in the front-rear direction L may be lower than the tensile load of the waist-around elastic member 45 in the width direction W. When wearing a tape-type diaper, in a state in which the back of the wearer is placed in the rear waistline region S2, the front waistline region is pulled while the crotch region is placed between both feet of the wearer, and the abdomen is covered by the front waistline region. When the diaper is pulled at the time of wearing, the leg-around elastic member 42 extends first, and then the waist-around elastic member 45 extends. The leg-around elastic members 42 is likely to extend and is more likely to fit the leg-around of the wearer. The leg-around elastic member 42 can be fitted to the body to suppress lateral leakage.

The tensile load of the leg-around elastic member 42 in the front-rear direction L may be lower than the tensile load of the waistband 80 in the width direction W. The leg-around elastic members 42 is likely to extend at the time of wearing and is more likely to fit the leg-around of the wearer, and the lateral leakage can be suppressed. In addition, the waistband 80 has a relatively high tensile load and is difficult to extend. Therefore, the waistband 80 less extends than the leg-around elastic member, and the position in the front-rear direction L is difficult to be shifted. Therefore, it is possible to suppress the waistband 80 from being shifted to the crotch side when the leg-around elastic member 42 extends, and to fit the leg-around elastic member 42 to the leg-around while maintaining the position of the waistband 80 in the front-rear direction. Therefore, both lateral leakage and rear leakage can be suppressed.

The tensile load of the waistband 80 in the width direction W, the tensile load of the waist-around elastic member 45 in the front-rear direction L, and the tensile load of the leg-around elastic member 42 in the width direction W can be measured as follows. A disposable diaper is disassembled using a cold spray, the waistband 80, the waist-around elastic member 45, and the leg-around elastic member 42 are taken out to prepare a sample. The sample is fixed between chucks of a tensile tester (for example, "RTA-100" manufactured by Orientec Co., Ltd.). A length of the sample in an initial state is a natural state. Then, the sample fixed between the chucks extends until the length becomes 1.5 times the length in the initial state, and the load at that time is set as a tensile load at the time of 1.5 times extension.

The disposable diaper 10 may satisfy S≥Y when the distance between the first proximal edge and the absorbent core 31 in the stretched state in the width direction W is set as S, and the length of the rising portion in the stretched state in the front-rear direction is set as Y. As illustrated in FIG. 2, S is the distance between the inner side edge 87I of the side joining portion 87 and the outer side edge 31E of the absorbent core 31 in the stretched state in the width direction W. As illustrated in FIG. 4, Y is the length of the non-joining portion 85 in the stretched state in the front-rear direction. The non-joining portion 85 serving as a rising portion of the waistband 80 is configured to rise with respect to the front end edge 84F of the joining portion 84 and the inner side edge 87I of the side joining portion 87, and forms an accommodation space for accommodating an excrement. At this time, since the distance S between the side joining portion 87 and the absorbent core 31 in the width direction W is equal to or greater than the length Y of the non-joining portion 85 in the front-rear direction L, it is possible to form a pocket such that the height of the accommodation space AS rising with respect to the outer side edge 31E of the absorbent core 31 is equal to or greater than the height of the accommodation space AS rising with respect to the joining portion 84. Therefore, the outer side edge of the accommodation space does not difficult to rise due to the rigidity of the absorbent core 31, and the entire accommodation space easily rises, and it becomes easy to secure the accommodation space. It is possible to secure an accommodation space of the pocket by the waistband 80 and suppress the occurrence of the rear leakage.

The disposable diaper 10 may satisfy S≤Y+U when the distance between the rear end edge of the absorbent core 31 and the second proximal edge in the stretched state in the front-rear direction is set as U. As illustrated in FIG. 4, U is the distance between the rear end edge 31R of the absorbent core 31 and the front end edge 84F of the joining portion 84 in the stretched state in the front-rear direction L. Since the front end edge 84F of the joining portion 84 is positioned on the rear side from the rear end edge 31R of the absorbent core 31, the front end edge 84F of the joining portion 84 may rise further toward the wearer side with respect to the rear end edge 31R of the absorbent core 31. At this time, the height of the rise of the accommodation space becomes Y+U. Since the height of the accommodation space by S is equal to or less than the height of the rise of the accommodation space by Y+U, it is possible to suppress the height of the rise of the accommodation space by Y+U. The region between the absorbent core 31 and the joining portion 84 is positioned between the rising fulcrum of the waistband 80 and the absorbent core 31, and has low rigidity and easy to deform as compared with both sides in the front-rear direction. By satisfying S≤Y+U, the region between the absorbent core 31 and the joining portion 84 is suppressed from being deformed due to the excessively high height of the rise of the accommodation space by Y+U, and it is easy to secure the accommodation space of the pocket.

The disposable diaper 10 may satisfy V≥U when the front end edge 85F of the non-joining portion 85 is positioned on the front side from the rear end edge 31R of the absorbent core 31, and the distance between the rear end edge 31R of the absorbent core 31 and the front end edge of the rising portion in the stretched state in the front-rear direction is set as V. As illustrated in FIG. 4, V is the distance between the rear end edge 31R of the absorbent core 31 and the front end edge 85F of the non-joining portion 85 in the stretched state in the front-rear direction L. In one or more embodiments in which the waistband and the absorbent core overlap with each other in a plan view, the distance V between the rear end edge 31R of the absorbent core 31 and the front end edge 85F of the non-joining portion 85 in the stretched state in the front-rear direction L becomes the length of the region overlapping with the absorbent core 31 in the rising portion in the front-rear direction. The length (V) of the region overlapping with the absorbent core 31 in the rising portion in the front-rear direction is equal to or longer than the length (U) of the region which does not overlap with the absorbent core 31 in the rising portion in the front-rear direction. In the region overlapping with the absorbent core in the rising portion, the absorbent core having high rigidity is positioned on the non-skin facing surface side as compared with the region which does not overlap with the absorbent core, and is more likely to rise on the wearer side. When V≥U is satisfied, the rising portion becomes easier to rise.

In addition, in the modified example, the disposable diaper 10 may satisfy U>V by positioning the front end edge 85F of the non-joining portion 85 on the front side from the rear end edge 31R of the absorbent core 31. The length (U) of the region which does not overlap with the absorbent core 31 in the rising portion in the front-rear direction L is longer than the length (V) of the region overlapping with the absorbent core 31 in the rising portion in the front-rear direction. In other words, the length of the rising portion disposed on the rear side from the rear end edge 31R of the absorbent core 31 in the front-rear direction L is longer than the length of the rising portion disposed on the front side of the rear end edge of the absorbent core in the front-rear direction L. Therefore, the pocket of the waistband can be formed larger on the rear side from the rear end edge 31R of the absorbent core 31. The user can grasp that the pocket of the waistband 80 is disposed larger on the rear side from the absorbent core, and can feel a sense of security with respect to the rear leakage.

A reinforcing sheet may be provided in a region (region U illustrated in FIG. 4) between the rear end edge 31R and the second proximal edge of the absorbent core 31 in the stretched state. In the present embodiment, a waist-around elastic member 45 is disposed as a reinforcing sheet. The rigidity of the region between the rear end edge 31R of the absorbent core 31 and the front end edge 84F (second proximal edge) of the joining portion 84 can be increased by the reinforcing sheet, so that the difference in the rigidity between the region overlapping with the absorbent core in the rising portion (region V illustrated in FIG. 4) can be reduced. Therefore, the entire rising portion is likely to rise.

In addition, in one or more embodiments in which the front end edge 85F of the non-joining portion 85 is positioned on the rear side from the rear end edge 31R of the absorbent core 31, U (the distance between the rear end edge 31R of the absorbent core 31 and the front end edge 84F of the joining portion 84 in the stretched state in the front-rear direction L) is set as Y (the length of the rising portion in the stretched state in the front-rear direction)+V (the distance between the rear end edge 31R of the absorbent core 31 and the front end edge of the rising portion in the stretched state in the front-rear direction). In one or more embodiments, when the entire pocket of the waistband is disposed on the rear side from the absorbent core, the user can feel a sense of security with respect to the rear leakage.

Even in one or more embodiments in which the front end edge 85F of the non-joining portion 85 is positioned on the rear side from the rear end edge 31R of the absorbent core 31, a reinforcing sheet may be provided in a region between the rear end edge 31R and the second proximal edge of the absorbent core 31 in the stretched state. The rigidity on the non-skin surface side of the waistband can be increased, and the rise of the waistband can be stabilized.

The waist-around elastic member 45 may be disposed in at least a part of a region between the rear end edge 31R of the absorbent core 31 and the front end edge 84F (second proximal edge) of the joining portion 84, and may be disposed in the entire region between the rear end edge 31R of the absorbent core 31 and the front end edge 84F (second proximal edge) of the joining portion 84 in the front-rear direction. In addition, the waist-around elastic member 45 may be disposed over the waistband 80 in the width direction Q. The rigidity is increased by the reinforcing sheet over the entire region of the waistband in the width direction, the rising portion over the entire region of the waistband in the width direction easily rises.

The disposable diaper 10 may satisfy U≤X, when the length of the joining portion 84 in the front-rear direction is set as X. When the disposable diaper is worn on the wearer in a sleeping state, the rear waistline region S2 may be inserted between the body of the wearer and the bedding or the like. At this time, since the length of the joining portion 84 in the front-rear direction is long, the rigidity of the joining portion 84 is increased, and the front end edge 84F of the joining portion 84 serving as the rising fulcrum of the rising portion can be suppressed from being tucked. Further, even if the front end edge 84F of the joining portion 84 is tucked, the length of the joining portion 84 in the front-rear direction is long, so that it is easy to secure the rising fulcrum of the rising portion. Therefore, it is easy to main-tain the rising fulcrum of the rising portion, and it is easy to secure the accommodation space of the pocket by the waistband 80. Further, the waist-around elastic member 45 as a reinforcing sheet may be disposed to straddle the front end edge 84F of the joining portion 84 serving as a rising fulcrum of the rising portion in the front-rear direction. It is possible to suppress the tucking of the front end edge 84F of the joining portion 84 serving as the rising fulcrum of the rising portion.

The length of the folded-back portion 86 in the front-rear direction L may be longer than the length of the non-joining portion 85 in the front-rear direction L in the stretched state. The length of the folded-back portion 86 in contact with the body in the front-rear direction is longer than the length of the non-joining portion 85 forming the accommodation space of the pocket. It is possible to secure a large area where the waistband 80 is in contact with the body, to enhance the stability of the shape of the waistband 80, and to suppress the occurrence of a gap between the waistband 80 and the body. Further, by increasing the length of the folded-back portion 86 in the front-rear direction, even if the contractive force of the folded-back portion 86 is increased, the contractive force per unit length can be suppressed. Therefore, the adhesion of the waistband 80 can be secured while suppressing the contact pressure of the folded-back portion 86 and suppressing the deterioration of feeling of wearing.

The rear end edge 86R of the folded-back portion 86 may be positioned on the rear side from the locking arrangement region R13 in the stretched state. The locking arrangement region R13 is easily brought into close contact with the body in a wearing state. The folded-back portion 86 is disposed on the waist opening 66 side from the locking arrangement region R13 which is in close contact with the body. The user can grasp that the pocket is disposed in the vicinity of the waist opening 66, and can feel a sense of security with respect to the rear leakage.

The inner side edge 87I of the side joining portion 87 of the waistband 80 may be positioned on the outer side from the leak-proof proximal edge 64 of the leak-proof gather 60 in the width direction W. The inner side edge 87I of the side joining portion 87 is susceptible to a force directed inward in the width direction W by contraction of the rising portion. Since the inner side edge 87I of the side joining portion 87 is positioned on the outer side from the leak-proof proximal edge 64 of the leak-proof gather 60 in the width direction W, the leak-proof proximal edge 64 by the contraction of the waistband 80 can be suppressed from moving inward the width direction W. The space interposed between the pair of leak-proof gathers can be widely provided, and the lateral leakage can be suppressed.

The contractive force of the folded-back portion 86 may be higher than the contractive force of the non-joining portion 85. Since an expansion and contraction stress of the folded-back portion 86 is relatively high, it is possible to secure the adhesion of the waistband 80 to the body. Further, since the stress of the region where the non-joining portion 85 is provided is relatively low, it is possible to prevent the pocket from excessively rising from the body when the stress of the non-joining portion 85 is high, and to suppress the occurrence of a gap between the body and the pocket.

The contractive force of the joining portion 84 may be lower than the contractive force of the non-joining portion 85 forming the rising portion. Since the contractive force of the joining portion 84 is low, the joining portion 84 is difficult to adhere to the body as compared to the non-joining portion 85. Since the joining portion is in close contact with the body, it is possible to prevent the rising portion which does not overlap with the joining portion 84 from being relatively separated from the body. Therefore, it is easy to secure the adhesion of the rising portion to the body. In addition, as illustrated in FIG. 6, the folded-back portion 86 also rises toward the wearer side together with the non-joining portion 85. At this time, the folded-back portion 86 in the region which does not overlap with the joining portion 84 does not come into close contact with the body together with the joining portion 84, and the rising property of the folded-back portion 86 can be maintained, and the accommodation space of the pocket can be secured. Further, in the folded-back portion 86 in the region overlapping with the joining portion 84, it is easy to adhere to the body together with the joining portion 84, and it is easy to secure the adhesion to the body.

For the measurement of the contractive force of the folded-back portion 86, the contractive force of the joining portion 84, and the contractive force of the non-joining portion 85, an autograph type tensile tester (for example, AG-1KN1) manufactured by Shimadzu Corporation can be used. First, in a state of extending the disposable diaper to the extent that wrinkles due to contraction action of the waistband 80 are eliminated, after measuring a dimension of the folded-back portion 86 in the width direction W, a dimension of the joining portion 84 in the width direction W, and a dimension of the non-joining portion 85 in the width direction W in advance (initial dimension), the waistband 80 is cut, and the folded-back portion 86, the joining portion 84, and the non-joining portion 85 are cut out to be used as samples.

Next, one end of each sample was interposed between fixed chucks and the other end was interposed between movable chucks, and a tensile load (N) when the sample was extended to a size of about 90% of the initial dimension at a speed of 300 mm/min, then inverted, and contracted to a size of about 75% of the initial dimension was obtained, and the tensile load was converted into a stress value (N/mm) per unit width (mm) and used as a contractive force.

Also, in a modified example, the rear end edge 86R of the folded-back portion 86 may be positioned on the front side from the rear end edge 84R of the joining portion 84 in the stretched state. Since the rear end edge 86R of the folded-back portion 86 is positioned on the front side from the rear end edge 84R of the joining portion 84, even in a case where the folded-back portion 86 is displaced at the time of manufacturing, it is possible to suppress the folded-back portion 86 from being unintentionally cut. When the folded-back portion 86 is unintentionally cut, it is possible to suppress the generation of cut pieces of the waistband 80.

In other modified examples, the waistband 80 may overlap with the fastening tape 90 in the thickness direction T. When pulling the fastening tape 90 at the time of wearing, the waistband 80 can be interlocked and pulled. Therefore, the waistband 80 more easily rises, thereby making it easier to form a pocket by the waistband 80.

Figure 7A:
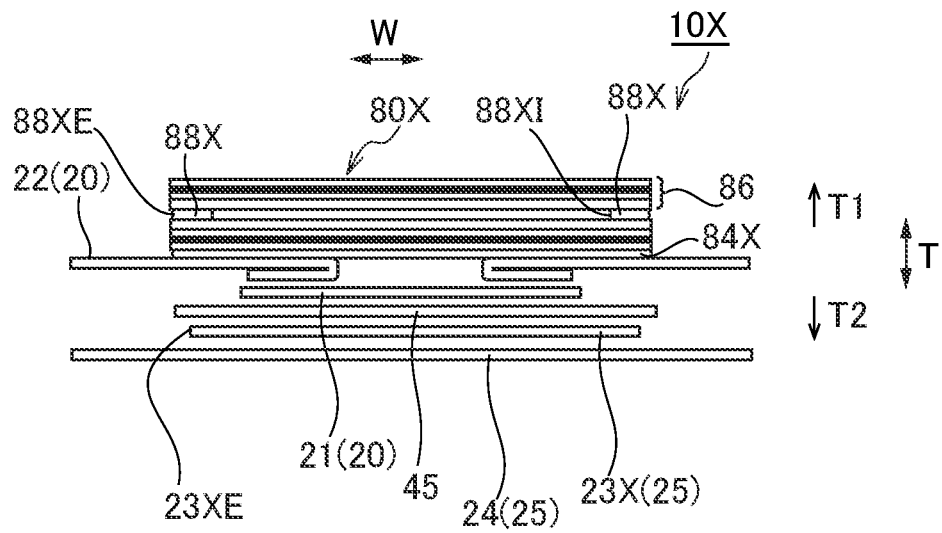
FIGS. 7A and 7B are schematic sectional views of a disposable diaper according to a second embodiment.
Figure 7B:
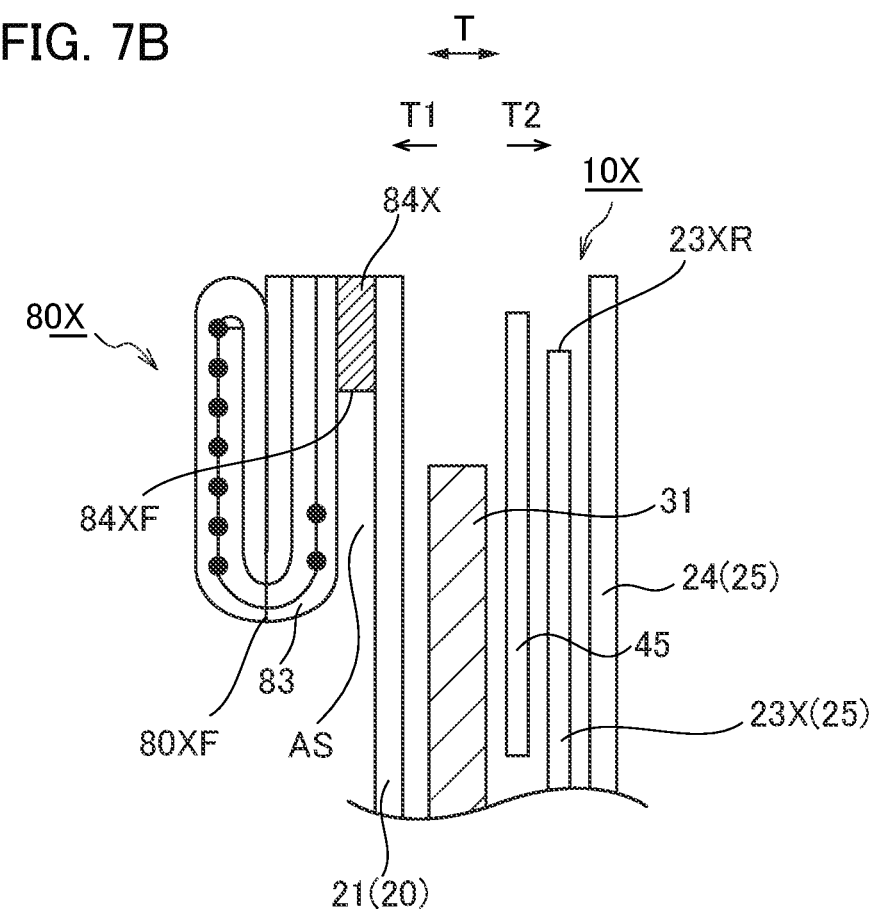

Next, a disposable diaper 10X according to a second embodiment will be described with reference to FIG. 7. In the description of the disposable diaper 10X according to the second embodiment, the same reference numerals are used to denote the same components as those of the first embodiment, and the description thereof will be omitted. FIG. 7 is a schematic sectional view of a disposable diaper according to the second embodiment. FIG. 7A is a sectional view of the disposable diaper 10X with reference to line 3A-3A illustrated in FIG. 1, and FIG. 7B is a sectional view of the disposable diaper 10X with reference to line 4A-4A illustrated in FIG. 1.

As illustrated in FIG. 7B, a rear end edge 23XR of a back-surface sheet 23X of the disposable diaper 10X according to the second embodiment may be positioned on the rear side from a front end edge 84XF of a joining portion 84X of a waistband 80X, at least a part of the back-surface sheet 23X may overlap with the joining portion 84X and the thickness direction T. That is, at least a part of the joining portion 84X and at least a part of the back-surface sheet 23X overlap with each other in a plan view of the disposable diaper. The front end edge 84XF of the joining portion 84X of the waistband 80X corresponds to the rear end edge of an accommodation space AS of the waistband 80X. The back-surface sheet 23X continues from a front waistline region S1 through a crotch region S3 to a rear waistline region S2, and suppresses the leakage of body fluid to a non-skin facing surface side T2 of the disposable diaper 10X. Since the back-surface sheet 23X overlaps with the joining portion 84X of the waistband 80X, it is possible to suppress the leakage of the body fluid from the accommodation space AS of the waistband 80X to the non-skin surface side of the disposable diaper 10X. Further, it is possible to increase the rigidity of the region where the joining portion 84X is provided by the back-surface sheet 23X, and a rising portion of the waistband 80X more easily rises with respect to the joining portion 84X, thereby more easily forming a pocket by the waistband 80X.

A length of the region where the back-surface sheet 23X and the joining portion 84X overlap with each other in the front-rear direction L may be 50% or more of the length of the joining portion 84X in the front-rear direction L. Even in a case where the body fluid oozes out from the accommodation space AS of the waistband 80X to the joining portion 84X, it is easy to suppress the leakage of the body fluid into the non-skin facing surface side T2 of the disposable diaper 10X. The region where the back-surface sheet 23X and the joining portion 84X overlap with each other may be provided over the entire region of the joining portion 84X in the front-rear direction L. It is possible to further suppress the leakage of the body fluids into the non-skin facing surface side T2 of the disposable diaper 10X. The rear end edge 23XR of the back-surface sheet 23X of the second embodiment is disposed on the front side from the rear end edge of the disposable diaper 10X; however, in a modified example, it may correspond to the rear end edge of the disposable diaper 10X.

As illustrated in FIG. 7A, an outer side edge 23XE of the back-surface sheet 23X may be positioned on the outer side from an inner side edge 88X1 of the second joining portion 88 of the waistband in the width direction W, and at least a part of the back-surface sheet 23X may overlap with a second joining portion 88X in the thickness direction T. The inner side edge 88X1 of the second joining portion 88X of the waistband 80X corresponds to the outer side edge of the accommodation space AS of the waistband. Since the back-surface sheet 23X overlaps with the second joining portion 88X, it is possible to suppress the leakage of the body fluid from the accommodation space AS of the waistband 80X to the non-skin facing surface side T2 of the disposable diaper. Further, it is possible to increase the rigidity of the region where the second joining portion 88X is provided by the back-surface sheet 23X, and a rising portion of the waistband 80X more easily rises with respect to the second joining portion 88X, thereby more easily forming a pocket by the waistband 80X.

A length of the region where the back-surface sheet 23X and the second joining portion 88X overlap with each other in the width direction W may be 50% or more of the length of the second joining portion 88X in the width direction W. Even in a case where the body fluid oozes out from the accommodation space AS of the waistband 80X to the second joining portion 88X, it is easy to suppress the leakage of the body fluid into the non-skin facing surface side T2 of the disposable diaper. The region where the back-surface sheet 23X and the second joining portion 88X overlap with each other may be provided over the entire region of the second joining portion 88X in the width direction LW. It is possible to further suppress the leakage of the body fluids into the non-skin facing surface side T2 of the disposable diaper. The outer side edge 23XE of the back-surface sheet 23X may be positioned on the inner side from the outer side edge 88XE of the second joining portion 88 in the width direction W. Even with this configuration, since at least a part of the back-surface sheet 23X overlaps with the second joining portion 88X in the thickness direction T, the leakage of the body fluid can be suppressed.

The back-surface sheet 23X may overlap with the waist-around elastic member 45 in the thickness direction T and may be disposed in the waist region R14. Both the waist-around elastic member 45 and the back-surface sheet 23 can increase the rigidity of the waist region R14 and suppress the rear leakage.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

According to one or more embodiments of the present invention, it is possible to provide a disposable diaper which can appropriately form a pocket due to a waistband and can suppress the occurrence of the rear leakage.

10, 10X: Disposable diaper
10F: Front end edge of disposable diaper
10R: Rear end edge of disposable diaper
20: Skin surface side sheet
21: Top-surface sheet
22: Side sheet
23: Back-surface sheet
24: Exterior sheet
25: Non-skin surface side sheet
31: Absorbent core
31R: Rear end edge of absorbent core
42: Leg-around elastic member
45: Waist-around elastic member (reinforcing sheet)
45F: Front end edge of waist-around elastic member
45R: Rear end edge of waist-around elastic member
60: Leak-proof gather
61: Leak-proof elastic member
65: Leg opening
66: Waist opening
80, 80X: Waistband
80F: Front end edge of waistband
80R: Rear end edge of waistband
81: Sheet layer
811: First nonwoven fabric layer
812: Second nonwoven fabric layer
813: Film layer
82: Band elastic member
83: Facing portion
83F: Front end edge of facing portion
83R: Rear end edge of facing portion
84: Joining portion
84F: Front end edge of joining portion (second proximal edge)
84R: Rear end edge of joining portion
85: Non-joining portion (rising portion)
85F: Front end edge of non-joining portion
85R: Rear end edge of non-joining portion
86: Folded-back portion
86R: Rear end edge of folded-back portion
87: Side joining portion
87I: Inner side edge of side joining portion (first proximal edge)
90: Fastening tape
90F: Front end edge of fastening tape
90R: Rear end edge of fastening tape
92: Base portion
93: Locking portion
93F: Front end edge of locking portion
93R: Rear end edge of locking portion
95: Target portion
FL: Fold line
R11: Tape arrangement region
R12: Waist opening region
R12CL: Center of waist opening region in front-rear direction
R13: Locking arrangement region
R14: Waist region
R14CL: Center of waist region in front-rear direction
R15: Space region
AS: Accommodation space
S1: Front waistline region
S2: Rear waistline region
S3: crotch region
T: Thickness direction
T1: Skin facing surface side
T2: Non-skin facing surface side
L: Front-rear direction
W: Width direction

What is claimed is:

1. A disposable diaper having a front-rear direction and a width direction which are orthogonal to each other, comprising:
a front waistline region;
a rear waistline region;
a crotch region disposed between the front waistline region and the rear waistline region;
an absorbent core;
a skin surface side sheet disposed on a skin facing surface side from the absorbent core;
a waistband disposed on the skin facing surface side of the skin surface side sheet in the rear waistline region; and
a fastening tape disposed in the rear waistline region, wherein
a facing portion disposed closest to the skin surface side sheet in the waistband and that comprises:
a joining region joined to the skin surface side sheet; and
a non-joining region to a front side from the joining region and not joined to the skin surface side sheet,
a space interposed between the non-joining region and the skin surface side sheet in the waistband forms a pocket that opens toward the front side,
a rear end edge of the waistband is disposed, in the front-rear direction in a waist region disposed on the rear side from a locking arrangement region extending in the width direction from a locking portion of the fastening tape, on a rear side from a center of the waist region, the waistband has a folded-back portion folded to a side away from the skin surface side sheet from a fold line, as a base point, extending in the width direction at a front end edge of the non-joining region, the non-joining region in the waistband comprises a band elastic member, the waistband comprises:
- a first nonwoven fabric layer;
- a second nonwoven fabric layer; and
- a film layer disposed between the first nonwoven fabric layer and the second nonwoven fabric layer, and the first nonwoven fabric layer, the second nonwoven fabric layer and the film layer are folded from the fold line, as a base point.

2. The disposable diaper according to claim 1, wherein the waistband has a second joining portion that joins the folded-back portion and the facing portion, and
an inner side edge of the second joining portion is disposed on an outer side from the absorbent core in the width direction.

3. The disposable diaper according to claim 2, wherein the waistband has a side joining portion joined to the skin surface side sheet on an outer side from the non-joining region, and
an inner side edge of the side joining portion is disposed on an outer side from the absorbent core in the width direction.

4. The disposable diaper according to claim 1, wherein at least a part of the non-joining region of the waistband overlaps with the absorbent core.

5. The disposable diaper according to claim 1, wherein
a plurality of the band elastic members is arranged at intervals in the front-rear direction, and is arranged in each of the folded-back portion and the non-joining region, and
a number of the band elastic members in the folded-back portion is larger than a number of the band elastic members in the non-joining region.

6. The disposable diaper according to claim 1, wherein a rear end edge of the waistband is disposed on the rear side of a center of a waist opening region in the front-rear direction in the waist opening region disposed on the rear side from a tape arrangement region extending from the fastening tape in the width direction.

7. The disposable diaper according to claim 1, wherein
the non-joining region is provided from the front end edge of the joining region to the fold line, and
a length of the folded-back portion in the front-rear direction is longer than a length of the non-joining region in the front-rear direction.

8. The disposable diaper according to claim 1, wherein the rear end edge of the folded-back portion is disposed on the rear side from the locking arrangement region.

9. The disposable diaper according to claim 1, wherein the rear end edge of the folded-back portion is disposed on the front side from the rear end edge of the joining region.

10. The disposable diaper according to claim 1, wherein a contractive force of the folded-back portion is higher than a contractive force of the non-joining region.

11. The disposable diaper according to claim 1, wherein the rear end edge of the non-joining region is disposed on the rear side from a center of the locking arrangement region in the front-rear direction.

12. The disposable diaper according to claim 1, wherein the front end edge of the joining region is disposed on the front side from the rear end edge of the locking arrangement region.

13. The disposable diaper according to claim 1, wherein the rear end edge of the joining region reaches a rear end edge of the disposable diaper.

* * * * *